(12) United States Patent
Klaffenbach (10) Patent No.: US 11,364,153 B2
(45) Date of Patent: Jun. 21, 2022

(54) ELECTRICALLY-HEATABLE PLASTER

(71) Applicant: LTS Lohmann Therapie-Systeme AG, Andemach (DE)

(72) Inventor: Peter Klaffenbach, Kaarst (DE)

(73) Assignee: LTS LOHMANN THERAPIE-SYSTEM AG, Andernach (DE)

( * ) Notice: Subject to any disclaimer, the term of this patent is extended or adjusted under 35 U.S.C. 154(b) by 702 days.

(21) Appl. No.: 15/564,361

(22) PCT Filed: Apr. 8, 2016

(86) PCT No.: PCT/EP2016/057756
§ 371 (c)(1),
(2) Date: Oct. 4, 2017

(87) PCT Pub. No.: WO2016/162481
PCT Pub. Date: Oct. 13, 2016

(65) Prior Publication Data
US 2018/0125723 A1   May 10, 2018

(30) Foreign Application Priority Data
Apr. 8, 2015   (EP) .................................... 15162818

(51) Int. Cl.
*A61F 7/00* (2006.01)
*A61F 13/00* (2006.01)
(Continued)

(52) U.S. Cl.
CPC .......... *A61F 13/0276* (2013.01); *A61F 7/007* (2013.01); *A61F 13/00063* (2013.01);
(Continued)

(58) Field of Classification Search
CPC .......... A61L 15/28; A61L 15/44; A61L 15/58; A61L 15/16; A61L 15/32; A61F 13/0276;
(Continued)

(56) References Cited

U.S. PATENT DOCUMENTS 5,766,236 A * 6/1998 Detty ...................... A61N 1/321
602/2
6,436,063 B1   8/2002 Augustine et al.
(Continued)

FOREIGN PATENT DOCUMENTS

CA         2044675        12/1991
DE   20 2013 006 258      10/2013
(Continued)

OTHER PUBLICATIONS

International Search Reportissued in corresponding International Appication No. PCT/EP2016/057756 dated Jul. 1, 2016, 3 pages.
(Continued)

*Primary Examiner* — Ophelia A Hawthorne
(74) *Attorney, Agent, or Firm* — Haug Partners LLP (57) ABSTRACT

An electrically-heatable plaster that comprises a self-adhesive skin contact layer, an electrically-conductive textile fabric in which electrically-conductive fibres are in contact with one another, as a heating element, and optionally at least one active substance, as well as to a method for production and the use of same for local heat therapy and/or transdermal application of active substances.

12 Claims, 1 Drawing Sheet

(51) Int. Cl.

| | |
|---|---|
| *A61F 13/02* | (2006.01) |
| *H05B 3/34* | (2006.01) |
| *A61L 15/42* | (2006.01) |
| *A61K 9/70* | (2006.01) |
| *A61K 9/00* | (2006.01) |
| *A61K 31/192* | (2006.01) |
| *A61K 31/196* | (2006.01) |
| *A61F 7/02* | (2006.01) |

(52) U.S. Cl.
CPC ........ *A61F 13/023* (2013.01); *A61F 13/0289* (2013.01); *A61K 9/0009* (2013.01); *A61K 9/7061* (2013.01); *A61K 31/192* (2013.01); *A61K 31/196* (2013.01); *A61L 15/42* (2013.01); *H05B 3/342* (2013.01); *A61F 2007/0071* (2013.01); *A61F 2007/0078* (2013.01); *A61F 2007/0093* (2013.01); *A61F 2007/0098* (2013.01); *A61F 2007/0226* (2013.01); *A61F 2007/0249* (2013.01); *A61F 2007/0261* (2013.01); *A61F 2013/002* (2013.01); *A61F 2013/00195* (2013.01); *A61F 2013/00646* (2013.01); *A61F 2013/00919* (2013.01); *A61F 2013/00936* (2013.01); *H05B 2203/015* (2013.01)

(58) Field of Classification Search
CPC ..... A61F 13/023; A61F 7/007; A61K 9/7061; A61K 9/7023; A61K 9/7038; A61K 9/7092; A61K 9/7046
See application file for complete search history.

(56) References Cited

U.S. PATENT DOCUMENTS

| | | | | |
|---|---|---|---|---|
| 7,238,196 | B2 * | 7/2007 | Wibaux | ................ H05B 3/342 |
| | | | | 607/152 |
| 7,854,712 | B2 * | 12/2010 | Evans | .................... D04B 21/14 |
| | | | | 602/6 |
| 2003/0186608 | A1 | 10/2003 | Goldberg | |
| 2005/0043658 | A1 | 2/2005 | Rix | |
| 2005/0096574 | A1 * | 5/2005 | Wibaux | ............ A61F 13/00063 |
| | | | | 602/2 |
| 2018/0125723 | A1 | 5/2018 | Klaffenbach | |

FOREIGN PATENT DOCUMENTS

| | | |
|---|---|---|
| EP | 0 212 096 | 3/1987 |
| EP | 0 463 516 | 2/1992 |
| EP | 3280371 | 10/2016 |
| JP | H8-001539 U | 11/1996 |
| JP | 2003-327527 | 4/2005 |
| JP | 2003327527 | 11/2019 |
| WO | WO 94/15668 | 7/1994 |
| WO | WO 99/15101 | 4/1999 |
| WO | WO 03/039417 | 5/2003 |
| WO | WO 2004/107816 | 12/2004 |
| WO | WO 2005/044141 | 5/2005 |
| WO | WO 2016/162481 | 10/2016 |

OTHER PUBLICATIONS

Japanese Office Action, dated Apr. 28, 2020 in corresponding Japanese Application No. 2017-552124 in English Translation, 8 pages.

Chinese Office Action dated May 24, 2021 in corresponding Chinese Application No. 201680022959.2 in English Translation, 9 pages.

Japanese Office Action dated Jan. 7, 2020 in corresponding Japanese Application No. 2017-552124 in English Translation.

Canadian Office Action and Examination Search Report dated Feb. 10, 2022 in corresponding Canadian Application No. 2,981,397, 3 pages.

* cited by examiner

ELECTRICALLY-HEATABLE PLASTER

The present application claims priority from International Patent Application No. PCT/EP2016/057756 filed on Apr. 8, 2016, which claims priority from European Patent Application No. EP 15162818.7 filed on Apr. 8, 2015, the disclosures of which are incorporated herein by reference in their entirety.

FIELD OF THE INVENTION

It is noted that citation or identification of any document in this application is not an admission that such document is available as prior art to the present invention.

The invention relates to plasters, including active substance plasters, and methods of manufacturing them. The invention relates, in particular, to adhesive and active substance plasters, which are electrically heatable.

Heat is considered to have a healing effect. Heat therapies thus belong to the oldest medicinal procedures. Differing from therapeutic hyperthermia, medicinal heat therapy is used locally, for instance with diseases of the locomotor system or overload damage. Heat is considered in the medical field to have, above all, the following effects: Muscle relaxation, improvement of the circulation, reduction of the viscosity of the synovial fluid, improvement of the extensibility of the collagenous connecting tissue and pain relief.

For local heat therapy, certain carriers, which have been previously heated, are commonly applied as latent heat stores for a number of minutes to a few hours onto the area of the body to be treated. Examples of latent heat stores are grain sacks, mud packs or heat storing gels. Heating cushions can, however, also be used for local heat therapy, the contents of which deliver heat for up to 24 hours by way of an accelerated oxidation process. Furthermore, specific skin receptors can also be stimulated with a carrier, for instance an ointment or a plaster, containing a capsaicin in order to produce a subjective feeling of heat.

Plasters are particularly suitable for local heat therapy because they can be fastened on or to the skin of a patient with their self-adhesive surface so that they do not slip, even when the patient moves, and maintain their contact with the surface of the skin of the patient.

It is also known that the supply of heat can improve the transdermal administration of a pharmaceutically active substance. However, latent heat stores used for these purposes do not allow a monitored and/or controllable supply of heat because, for instance, neither a precise setting of a target temperature nor the constant maintenance of a predetermined target temperature over a longer period of time up to a few hours is possible. If the latent heat store is fixedly integrated into a plaster, interrupting the supply of heat without having to remove the plaster from the skin of the patient is not possible.

It was therefore the object of the present invention to provide a plaster for the local supply of heat, wherein the plaster enables a controllable temperature management even for more than a few hours without having to remove the plaster from its application site.

The publication WO 99/15101 A1 discloses a multi-layer wound dressing with the properties of promoting wound healing and pain relief. This wound dressing includes at least one good electrically conductive layer, which is flexible and is composed of silver-plated fibres and non-metallised fibres.

The published specification WO 03/039417 A2 discloses a heatable wound dressing, which includes an electrically conductive textile heating element and a control circuit for controlling the electrically conductive textile. The electrically conductive textile comes either directly into contact with the skin of the patient or the layer coming into contact with the skin of the patient is arranged adjacent to it.

The publication WO 94/15668 A1 describes an electrical stimulation body pack with a flexible pocket, which is constituted by an electrically insulating cloth, and a device for receiving a heat transfer medium. The pocket has a first surface with a moisture barrier for separating a cooled heat transfer medium from a body in contact with it and a second surface with an insulating device for separating a heated heat transfer medium from a body in contact with it in order to prevent skin burns. The device for arranging and pressing the first surface of the flexible pocket against a body part is so constructed that it presses either the first or the second surface of the flexible pocket against a body part. The body pack further has a flexible electrical nerve and muscle stimulation electrode, which is fastened to the flexible pocket in a position which enables direct contact between the stimulation electrode and the body part when either the first or second surface of the flexible pocket is pressed against the body part, wherein a conductive wire is electrically connected to the flexible nerve and muscle stimulation electrode.

US 2003/0186608 A1 discloses a fabric with pain relieving properties, which is produced from an electrically conductive thread and an electrically non-conductive thread. The fabric can be incorporated into textile products, such as bandages, support bandages and clothing.

The publication WO 2004/107816 A1 discloses an apparatus which is suitable for the topical administration of an active substance and includes a breathable heating element. The breathable heating element is a metallised fabric. The laminar heating element is applied to a skin or wound contact layer and is covered by an adhesive layer. The heating element is a wound metallic conductive track in an etched fabric. The skin contact layer can contain a microencapsulated active substance, which can be liberated by heat activation from the microcapsules, which are then melting, and supplied to the skin. The wound metallic conductive track constituting a heating element results, however, in a heat distribution, which is not sufficiently homogenous.

Electrically conductive textiles with a three-dimensional fibre distribution are proposed in DE 20 2013 006 258 U1 as an apparatus for producing heatable surfaces for the uniform heating of plastic moulds in the manufacture of thermoplastic or duroplastic fibre plastic composite components.

SUMMARY OF THE INVENTION

It was therefore the object of the present invention to provide a plaster, which is capable of producing heat, wherein the heat distribution over the surface, particularly the skin contact surface of the plaster, is as homogenous as possible.

The object is solved in accordance with the first aspect of the invention by an electrically heatable plaster, which includes a self-adhesive skin contact layer and an electrically conductive textile sheet, in which electrically conductive fibres are in contact with one another.

In accordance with a second aspect, the invention relates to a method for the manufacture of electrically heatable plasters, which include a self-adhesive skin contact layer and an electrically conductive textile sheet, in which electrically conductive fibres are in contact with one another.

According to a third aspect, the invention relates to the use of an electrically conductive textile sheet, in which electrically conductive fibres are in contact with one another, for the manufacture of electrically heatable plasters.

In accordance with a further aspect, the invention relates to the use of electrically heatable plasters including a self-adhesive skin contact layer and an electrically conductive textile sheet, in which electrically conductive fibres are in contact with one another, for local heat therapy.

In accordance with a further aspect, the invention relates to the use of electrically heatable plasters including a self-adhesive skin contact layer and an electrically conductive textile sheet, in which electrically conductive fibres are in contact with one another, to improve skin permeation for an active substance contained in the plaster.

In accordance with a further aspect, the invention relates to the use of plasters including a self-adhesive skin contact layer and an electrically conductive textile sheet, in which electrically conductive fibres are in contact with one another, for the administration of at least one active substance contained in the plaster to and/or over the skin of a mammal.

In accordance with a further aspect, the invention relates to methods for the administration of heat and/or at least one active substance to and/or over the skin of a mammal by means of an electrically heatable plaster, which includes a self-adhesive skin contact layer and an electrically conductive textile sheet, in which electrically conductive fibres are in contact with one another.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The term plaster in accordance with the first aspect is to be understood as laminar, flexible, preferably self-adhesive elements, which can be applied on or to the skin of a mammal, preferably a human being. In the context of the present disclosure, the term "plasters" includes not only so-called adhesive plasters but also so-called medicinal plasters. Adhesive plasters are adhesive textile strips, which are commonly used for fixing dressings or articles to the skin of a patient. Medicinal plasters are to be understood as laminar, flexible, preferably self-adhesive elements, which contain at least one pharmaceutical active substance, which is liberated from it after application of the medicinal plaster and is administered to or over the skin of the patient.

In the context of the present invention, plasters do not serve to cover wounds but are fastened to in-tact skin. The term "plaster" in the context of the present invention thus includes no prefabricated quick wound dressings, in which a piece of dressing is connected with an adhesive strip of textile or plastic material.

The plaster in accordance with the first aspect is an electrically heatable plaster. This means that the plaster can generate heat when an electric current flows through at least one portion or component of the plaster.

The plaster in accordance with the first aspect includes a self-adhesive skin contact layer and an electrically conductive, textile sheet, in which electrically conductive fibres are in contact with one another. The self-adhesive skin contact layer is the layer of the plaster with which it is fastened to or on the skin of a patient. The skin contact layer includes or consists of a skin-compatible adhesive. The skin-compatible adhesive can be selected from the group of adhesives which includes polyacrylates, polymethacrylates, silicones, polyisobutylenes and mixtures thereof.

The plaster further includes an electrically conductive textile sheet, in which electrically conductive fibres are in contact with one another. This sheet is capable of generating heat if it is part of an electrical current circuit and electrical current flows through it. The electrically conductive textile sheet is flexible and can thus adapt to the contour of the surface to which the plaster is adhered so that as uniform as possible a heating of the skin area can be ensured and the plaster is not perceived by the patient as an excessively intrusive foreign body.

In one embodiment of the plaster, the electrically conductive textile sheet, in which electrically conductive fibres are in contact with one another, constitutes the rear layer of the plaster. This embodiment represents the simplest construction of the plaster, which may be made comparatively simply and economically.

In an alternative embodiment, the plaster includes a self-adhesive skin contact layer, an electrically conductive textile sheet and additionally a rear layer. In this embodiment, the electrically conductive textile sheet, in which electrically conductive fibres are in contact with one another, does not constitute the rear layer of the plaster. In this embodiment, the electrically conductive textile sheet is an additional sheet. This embodiment is particularly advantageous in embodiments of plasters in accordance with the invention which contain a pharmaceutical active substance because the rear layer can be selected such that it is impermeable to the active substance.

In accordance with an additional and/or alternative embodiment, the additional rear layer is a textile sheet or a polymer film, preferably a polymer film impermeable to the active substance. In a further embodiment, the sheet is knitted structure of natural fibres, of synthetic fibres or of a mixture of natural and synthetic fibres. In accordance with another embodiment, the polymer film is perforated. The textile sheet or a perforated polymer film as the rear layer of the plaster impairs the gas exchange or the supply of oxygen to the skin less than a rear layer of a non-perforated polymer film.

In an additional and/or alternative embodiment, the plaster includes a heat insulating layer. A heat insulating layer ensures that the heat generated with the plaster is supplied substantially in the direction of the skin. The free surface of the plaster, after application of the plaster, heats up less strongly, which is perceived by the patient as pleasant. Furthermore, less electrical energy is required in order to maintain a predetermined temperature. Thus a given power source can be used longer or power sources of lower power can be used, which are commonly also smaller and/or lighter.

The heat insulating layer is arranged in the plaster on the surface of the electrically conductive textile sheet remote from the skin of the patient. In one form of this embodiment, the rear layer of the plaster is constructed as a heat insulating layer, particularly in embodiments of plasters in which the electrically conductive textile sheet does not constitute the rear layer of the plaster. In an alternative form of the embodiment, the heat insulating layer is a layer which is present in addition to the rear layer and is thus arranged between the electrically conductive textile sheet and the rear layer. A plaster in accordance with this embodiment thus has a self-adhesive skin contact layer, an electrically conductive textile sheet, a heat insulating layer and a rear layer.

The heat insulating layer can, for instance, be a layer of a polymer foam. The polymer foam for the heat insulating layer can be an open pored foam, that is to say a polymer foam in which the pores have an open connection with one another, or a closed pore foam, in which the individual pores are not openly connected to one another.

In an additional and/or alternative embodiment, the plaster has a removable protective layer, which covers the self-adhesive skin contact layer of the plaster before it is used. The removable protective layer must be removed from the self-adhesive surface of the plaster before it is used.

In accordance with an additional and/or alternative embodiment, the electrically conductive textile sheet is arranged between the self-adhesive skin contact layer and the rear layer. In another embodiment, the electrically conductive textile sheet is embedded in the self-adhesive skin contact layer.

The electrically conductive textile sheet is a textile sheet with a three-dimensional fibre distribution. This means that the fibres cross or overlap in the textile sheet. The electrically conductive fibres of the textile sheet are thus in contact with one another in the textile sheet so that an electrical current can flow over the entire area of the textile sheet and can warm the textile sheet as uniformly as possible. The term "are in contact with one another" includes not only the direct mutual touching of electric fibres at their intersection points but also designs in which an electrically conductive material is situated at the intersection points between two crossing electrical conductive fibres of the textile sheet.

The textile sheet is preferably a fabric, a knitted structure, a crocheted structure, a braided structure, a bidirectional or multidirectional fabric, a felt or a fleece (fibre fleece or spun fleece) of fibres.

In accordance with a preferred embodiment, the fabric is a fabric in plain weave, twill weave or satin weave. The fabric is particularly preferably a five-harness or eight-harness satin weave. The advantage of satin weave resides on the one hand in that it is particularly conformable and on the other hand can be arranged in the plaster oriented so that as high as possible a number of electrically conductive fibres are situated as close as possible to the surface of the plaster, which comes into contact with the skin of the patient.

In an alternative and/or additional embodiment, the electrically conductive textile sheet is selected from the group of textile sheets which consists of
  (a) exclusively electrically conductive fibres;
  (b) mixtures of electrically conductive and electrically non-conductive fibres; and
  (c) one or more electrically non-conductive textile sheets, which is/are equipped with adhesive, electrically conductive binder(s) and electrically conductive particles, preferably metal particles, which are three-dimensionally and durably fixed in the textile sheet.

"Electrically conductive fibres" are to be understood as fibres which can conduct electrical current. Electrically conductive fibres are, for instance, fibres which consist of an electrically conductive material, for instance a metal, an alloy or an electrically conductive plastic material. The term "electrically conductive fibres" is, however, also to be understood as fibres which include at least one electrically conductive core, which is sheathed by an electrically non-conductive material. The at least one electrically conductive core of the electrically conductive fibres consists of an electrically conductive material, for instance a metal, an alloy or an electrically conductive plastic material. The term "electrically conductive fibres" is also to be understood as fibres which include at least one electrically non-conductive core, which is sheathed with an electrically conductive material. The electrically conductive material for the electrically conductive sheath can be a metal, an alloy, or an electrically conductive plastic material. An example of such fibres is polyamide fibres sheathed with silver.

The plaster in accordance with the first aspect of the invention is an electrically heatable plaster. This means that by the application of an electrical voltage to the electrically conductive textile sheet of the plaster and the resultant current flow heat can be produced. The temperature, which may be produced with the electrically conductive textile sheet, preferably measured at the surface of the electrically conductive textile sheet, at a given voltage or current density may be adjusted by the nature and proportion of the electrically conductive fibres in the electrically conductive textile sheet or in the mixture of electrically conductive or metal-sheet fibres and the non-electrically conductive fibres. In general, it is the case that the smaller the proportion of electrically conductive fibres and/or particles in the electrically conductive textile sheet the higher is the temperature to be achieved.

Alternatively and/or additionally, the degree of the heating with a given, electrically conductive textile sheet, may be adjusted by means of the voltage and/or the current density, which is applied to the electrically conductive textile sheet. In accordance with one embodiment, the voltage which is applied to the electrically conductive textile sheet during the application of the plaster is at least 1.35 V and preferably less than 3.6 V, particularly preferably less than 3.0 V. When using conventional batteries, the voltage is, dependent on the battery, about 1.35 V, about 1.4 V, about 1.5 V, about 1.55V or about 3.0 V.

In one embodiment, the heating of the electrically conductive textile sheet can be so adjusted that the temperature, measured at the surface of the electrically conductive textile sheet, does not exceed a value of 50° C. The heating of the electrically conductive textile sheet is preferably so adjusted that the temperature, measured at the surface of the electrically conductive textile sheet, does not exceed a value of 45° C., preferably a value of 40° C., particularly preferably a value of 37° C., most particularly preferably a value of 35° C. and most extremely preferably a value of 32° C.

The sheet or surface resistance of the electrically conductive textile sheet and thus the heating time at a given voltage and heating area can be adjusted in an application-specific manner by selection of the electrically non-conductive fibre component.

The higher the proportion of electrically non-conductive fibres in the mixture of electrically conductive or metal-sheathed fibres and electrically non-conductive fibres, the longer is the heating time with a given voltage and heating area in order to achieve a predetermined surface temperature on the textile sheet.

In accordance with an additional and/or alternative embodiment, the electrically conductive textile sheet is embedded in a resin layer or a polymer layer. In accordance with another additional and/or alternative embodiment, the electrically conductive textile sheet is impregnated or saturated with a resin or a polymer.

In accordance with an additional embodiment, the resin or the polymer includes at least one electrically conductive filler. The at least one electrically conductive filler can be selected from the group which consists of graphite, soot, carbon nanotubes and metal particles. As a result of the at least one electrically conductive filler, an electrically conductive sheet is produced on the basis of a resin or polymer, with which a particularly homogenous heat distribution over the surface of the (textile or textile-reinforced) sheet can be achieved.

In an additional and/or alternative embodiment, the electrically conductive textile sheet is provided at suitable positions with electrodes, by means of which contact of the electrically conductive textile sheet with a voltage source and/or an electronic component to control the power supply electrically conductive textile sheet can occur.

The contact of the electrically conductive textile sheet with electrodes can be effected by sewing, welding or gluing the electrodes to/onto the electrically conductive textile sheet. The contact should be effected such that the contact resistance between the electrical contact and the electrically conductive textile is as small as possible in order reliably to prevent energy losses and positions with stronger heating. The electrodes are preferably arranged in the form of parallel conductors on the electrically conductive textile sheet.

In an additional and/or alternative embodiment, the plaster includes voltage source, which is electrically connectable to the electrically conductive textile sheet. The voltage source is preferably a direct current source. The direct current source can be a battery. So-called button cells are particularly suitable, that is to say electrochemical cells with a round cross-section, whose overall height is smaller than the diameter. Examples of suitable button cells are:

| Cell Type | IEC Designation | Example | Voltage |
|---|---|---|---|
| Mercury oxide-zinc cell | MR | MR52 | 1.35 V |
| Zinc-air cell | PR | PR41 | 1.4 V |
| Alkali-manganese cell | LR | LR44, L1154 | 1.5 V |
| Silver oxide-zinc cell | SR | SR44, SR1154 | 1.55 V |
| Lithium-manganese dioxide cell | CR | CR2032 | 3.0 V |
|  |  | CR2450 | 3.0 V |
| Lithium-carbon monofluoride cell | BR | BR2016 | 3.0 V |

In an additional and/or alternative embodiment, the plaster includes a switch, with which the current circuit between the electrically conductive textile sheet and the voltage source can be closed and/or interrupted again. In this embodiment, the plaster can, after its application to the skin of the patient, generate heat at any desired time and the generation of heat can be interrupted when required without the plaster having to be removed from the skin.

In an additional and/or alternative embodiment, the plaster includes, in addition to a voltage source, an insulating strip, which interrupts the current circuit between the voltage source and the electrically conductive textile sheet. This insulating strip consists of an electrically non-conductive material, preferably an electrically non-conductive plastic material. The insulating strip is arranged to be removable. This means that the insulating strip may be pulled out without a cover or the like having to be opened and as a result of the removal of the insulating strip the current circuit between the voltage source and the electrically conductive textile sheet is closed. This insulating strip can be removed directly before use of the plaster.

In an additional and/or alternative embodiment, the plaster includes a control and regulating electronic system, with which the temperature of the textile sheet can be maintained constant.

In an additional and/or alternative embodiment, the plaster includes an optical function display. The optional function display serves to indicate to the user that the plaster is functioning properly. The optional function display can be a light diode, which illuminates so long as the current circuit between the voltage source and the electrically conductive sheet is closed and electrical current is flowing. An alternative and/or additional optical function display can be a temperature measuring strip, which indicates the temperature, preferably the temperature of the surface of the electrically conductive textile sheet.

In accordance with an additional and/or alternative embodiment, the plaster includes at least one pharmaceutical active substance. Plasters containing a pharmaceutical active substance are also referred to as transdermal therapeutic systems or active substance plasters. These are devices which are suitable for supplying an active substance, preferably a pharmaceutical substance, for a longer period of time at a constant or at least approximately constant rate to and over the skin of the user/patient.

In one embodiment of the active substance-containing plaster, the self-adhesive skin contact layer is constituted by a self-adhesive polymer matrix, which also contains the at least one active substance or at least one of the active substances. In an additional and/or alternative embodiment, the self-adhesive skin contact layer is a separate self-adhesive contact layer, which can contain the at least one active substance but does not function as an active substance reservoir or plaster. The separate self-adhesive layer is applied to at least one region of the surface on the skin side of an active substance reservoir, which is additionally present.

The at least one active substance reservoir of a transdermal therapeutic system is either a polymer matrix, in which at least one active substance is contained, or a bag-shaped reservoir, which is defined by a sheath and contains a substantially liquid active substance preparation. The term "liquid" includes low viscosity, high viscosity and gel-like preparations. The sheath of the bag-shaped reservoir includes, at least on its side to be directed towards the skin, a semipermeable membrane, via which the active substance contained in the reservoir can be supplied and which optionally has a function controlling the release rate of the active substance. If the at least one active substance is contained in a polymer matrix of the transdermal therapeutic system, this polymer matrix is to be regarded as an active substance reservoir.

The active substance-containing plaster contains at least one active substance, preferably at least one pharmaceutical active substance. The pharmaceutical active substance can be any desired, transdermally administrable pharmaceutical active substance. For instance, the at least one pharmaceutical active substance can be selected from the group which includes non-steroidal antirheumatic drugs (NSAID's), anticholinergic drugs, parasympatholytic drugs, antimycotic drugs, MAO-B inhibitors, serotonin antagonists, alpha2-receptor agonists, photosensibilitators, hormones and/or proteins.

The non-steroidal antirheumatic drugs (NSAR or NSA), also non-steroidal antiphlogistic (NSAP) or NSAID (non-steroidal anti-inflammatory drugs), are painkillers (non-opioid analgesics), which are used in a symptom-related matter also for rheumatism therapy due to their anti-inflammatory (antiphlogistic) effect. In one embodiment, the non-steroidal antirheumatic drug is selected from the group, which consists of anthranilic acid derivatives, for instance mefenaminic acid, flufenamic acid, etofenamate and meclofenamic acid, selective COX-2 inhibitors, for instance celecoxib, etoricoxib, rofecoxib, lumiracoxib and valdecoxib, acetic acid derivatives and arylacetic acid derivatives, for instance aceclofenac, acematimine, bufexamac, diclofenac, etodolac, indometamine and ketorolac, oxicams, for instance lornoxicam, meloxicam, piroxicam and tenoxicam, propionic acid derivatives, for instance ibuprofen, dexibuprofen, naproxen, ketoprofen, dexketoprofen, flurbiprofen, benoxaprofen and tiaprofenic acid, salicylates, for instance acetyl salicylic acid, calcium carbasalate, lysine acetylsalicylate and salicylic acid and nabumetone and nimesulide.

The at least one pharmaceutical active substance is present in the form of its free base and/or at least one of its pharmaceutically acceptable salts. The term "pharmaceutically acceptable salt" also includes pharmaceutically acceptable acid addition salts of the active substance. If the at least one active substance is a chiral substance, the active substance is present either in the form of a racemate or in the form of its pharmaceutically active enantiomer in the transdermal therapeutic system.

In an additional and/or alternative embodiment, the transdermal therapeutic system includes at least one permeation enhancer, which improves the permeation of the at least one active substance through the skin of the patient.

In one embodiment, the active substance-containing plaster includes an active substance-impermeable rear layer. The active substance-impermeable rear layer consists commonly of a polymer film, which is impermeable to the active substance contained in the plaster. The active substance-impermeable rear layer provides protection for the active substance-containing layer. The rear layer additionally prevents the patient or another person unintentionally coming into contact with the active substance contained in the plaster and ensures that the active substance is released in a directed manner onto the skin of the patient.

Transdermal therapeutic systems are complex delivery forms, in which partially opposing requirements must be fulfilled. For instance, the active substance content in the transdermal therapeutic system must be large enough in order to be able to supply an amount of active substance necessary for the therapeutic benefit per unit time for a relatively long period of time. In this connection, there are however limits to the size of a transdermal therapeutic system, caused in particular by requirements in manufacture, handling and patient compliance.

In order to improve the transdermal administration of an active substance, so-called permeation enhancers, for instance, can be used. These are substances which are contained in the transdermal therapeutic system and make the skin more permeable to the active substance also contained in the plaster. In one embodiment, the active substance-containing plaster additionally includes at least one permeation enhancer and/or at least one pharmaceutically acceptable excipient.

However, the use of permeation enhancers can be accompanied by undesired side effects, such as skin irritations. Without excluding the use of permeation enhancers and/or other pharmaceutically acceptable excipients in the plaster, the electrically heatable plaster enables an improvement in the skin permeation of an active substance contained in the plaster by heating the skin area, in which the active substance is to be administered percutaneously with the aid of the electrically heatable plaster. The content of permeation enhancer in the plaster can thus, if appropriate, be smaller than in a comparable non-heatable plaster in order to achieve the same permeation rate.

In one embodiment, the electrically conductive textile sheet is arranged between the active substance-containing sheet and the active substance-impermeable rear layer of the active substance-containing plaster.

In an alternative embodiment, the electrically conductive textile sheet is separated from the active substance-containing layer by an active substance-impermeable layer.

In accordance with the second aspect, the invention relates to a method of manufacturing electrically heatable plasters in accordance with the first aspect, that is to say electrically heatable plasters, which include a self-adhesive skin contact layer and an electrically conductive textile sheet, in which electrically conductive fibres are in contact with one another.

In one embodiment of the method, the manufacturing method includes at least the following steps:
the provision of an electrically conductive textile sheet,
the lamination of the electrically conductive textile sheet onto a self-adhesive layer,
the separation of the individual plasters, and
the attachment of the contacts to the non-laminated side of the electrically conductive textile sheet.

In an additional and/or alternative embodiment, the method also includes laminating at least one further layer. In one form of this embodiment, the at least one further layer is a polymer film, a perforated polymer film or a textile sheet, such as textile, knitted structure, fabric or fleece or a layer of an open pore foam material or a closed pore foam material, which is preferably applied to the surface of the electrically conductive, textile sheet which is remote from the self-adhesive layer, which constitutes the skin contact layer of the plaster. In another and/or additional embodiment, the at least one further layer is a polymer layer, which is arranged, for instance, as an active substance-containing reservoir between the self-adhesive layer and the electrically conductive, textile sheet.

An additional and/or alternative embodiment method includes mounting of a voltage source and/or an on-off switch and/or an insulating strip.

In one embodiment of the method, the self-adhesive adhesive layer includes no pharmaceutical active substance. In an alternative embodiment, the self-adhesive adhesive layer includes at least one pharmaceutical active substance and optionally at least one permeation enhancer and/or at least one pharmaceutically acceptable excipient.

In an additional and/or alternative embodiment, the self-adhesive adhesive layer is attached, before the lamination of the electrically conductive textile sheet, to a polymer film, which constitutes, for instance, the removable protective film of the finished plaster.

The method of manufacturing the plaster commonly includes the provision of the individual layers or strata of the plaster before connecting them together in the form of rolls or sheet material. The different sheets are laid on one another in the manufacturing process and connected together to form a laminate. The separation of the plasters from the sheet-shaped laminated can be effected by stamping or by cutting.

In accordance with the third aspect, the invention relates to the use of an electrically conductive textile sheet in which electrically conductive fibres are in contact with one another, to manufacture electrically heatable plasters, preferably for manufacturing electrically heatable plasters which contain at least one pharmaceutical active substance.

As a result of the use of an electrically conductive textile sheet as the heating element in a plaster, a homogenous heat distribution can be achieved so that despite low voltages, a small spacing of the heating element from the skin of the patient and optionally only a slight increase of the temperature to a temperature, which is only a few degrees above the temperature of the skin surface of the patient, no undesired inhomogeneities occur in the temperature distribution over the surface of the plaster. A particularly uniform heating of the skin and a particularly good therapy outcome can thus be achieved.

According to one of the further aspects, the invention relates to the use of the electrically heatable plasters described above, which include a self-adhesive skin contact layer and a textile sheet, in which electrically conductive fibres are in contact with one another, for local heat therapy. The invention thus extends also to methods for local heat therapy, in which one of the plasters described above is used, preferably a plaster free of active substance, which includes a self-adhesive skin contact surface and an electrically conductive textile sheet, in which electrically conductive fibres are in contact with one another.

According to another of the further aspects, the invention relates to the use of the plasters described above, which include a self-adhesive skin contact layer and an electrically conductive textile sheet, in which electrically conductive fibres are in contact with one another, to improve the skin permeation of an active substance contained in the plaster. The invention thus extends also to methods for increasing the skin permeation for an active substance, preferably for a pharmaceutical active substance, in which a plaster in accordance with the first aspect is used, which has a self-adhesive skin contact layer, an electrically conductive textile sheet, in which electrically conductive fibres are in contact with one another, and an active substance.

According to another of the further aspects, the invention relates to the use of plasters as described above, which include a self-adhesive skin contact layer, an electrically conductive textile sheet, in which electrically conductive fibres are in contact with one another, and at least one active substance, for administering the at least one active substance to and/or over the skin of a mammal. The invention thus extends to methods for the transdermal administration of an active substance, preferably a pharmaceutical active substance, in which a plaster, which contains the active substance and is electrically heatable is fastened on or to the skin of a patient.

In the use of the plaster in accordance with the invention, the textile sheet functions as a heating element with which the plaster and the area of skin of the patient covered by the plaster is heated. In the use, the utilisation of the heat is important and not the action of the electric current per se necessary for the heating of the textile sheet the body or the area of the body covered by the plaster. In this respect, the use in accordance with the invention of the plasters in accordance with the invention differs from the interference current-regulation therapy, in which the healing of wounds, for instance injuries in the epithelium or also operational wounds within the body of a patient is accelerated by means of electrostimulation in combination with conventional wound care by comparison with standard wound care.

With the uses and/or methods in accordance with the further aspects of the invention, the current circuit between a voltage source and the electrically conductive, textile sheet is closed directly before or after the plaster is fastened on or to the skin of a mammal, preferably a human being. As a result of closing the current circuit, electric current flows through the electrically conductive, textile sheet, which heats as a consequence as a result of the applied voltage and its resistance. The heating has a therapeutic effect or results in an increase in the skin permeation of an active substance potentially contained in the plaster.

Exemplary Embodiments

Example 1

Ibuprofen-Plaster with an Electrically Heatable Rear Layer 174.32 g Durotak 387-2353 (solids content 37%) was diluted with 8.07 g ethylacetate and 31.6 g of a solution of 10% potassium hydroxide in methanol was added. After thorough mixing, 16.63 g oleic acid was added. 1.2 g aluminium acetyl acetonate and 1 g acetyl acetone were then added. After all the components were well mixed together, 16.63 g ibuprofen (racemate) was added. The composition was stirred at room temperature until all the components were completely dissolved. The adhesive composition was then spread out on a siliconized PET film 100 µm by means of a scraper so that a dry weight of 60 g/m$^2$ was achieved. The solvents were evaporated at ca. 80° C. The laminate was then covered with the heatable fibre material which was a spun fleece with electrically conductive fibres.

Example 2

Diclofenac Plaster with an Electrically Heatable Rear Layer 94.92 g Durotak 387-2287 (solids content 50%) was mixed with a solution of 0.72 g aluminium acetyl acetonate in 13 g ethyl acetate. 0.12 g α-tocopherol dissolved in 0.4 g ethyl acetate was added to this composition and homogeneously stirred. 2.4 g diclofenac-Na was dissolved in 5.4 g methanol and added to the composition. The composition was stirred at room temperature until the solids had completely dissolved. The adhesive composition was spread out onto a siliconized PET film 100 µm by means of a scraper such that a dry weight of 80 g/m$^2$ was achieved. The solvents were evaporated at ca. 75° C. The laminate was then covered with the heatable fibre material which was a spun fleece with electrically conductive fibres.

Example 3

Diclofenac Plaster with an Electrically Heatable Rear Layer 118.57 g Durotak 387-2051 (solids content 50%) was neutralised with 24 g of a solution of 2.4 g potassium hydroxi9de in 21.6 g methanol. 90.66 g of the thus neutralised adhesive solution was mixed with 2.26 g of a solution of 0.3 g aluminium acetyl acetonate in 1.75 g methanol and 0.3 g ethyl acetate. 7.5 g oleic acid and 0.25 g α-tocopherol were added and stirred to complete dissolution. 6.38 g of the solution of 2.0 g diclofenac-Na in 4.38 g methanol was added to it. The composition was stirred at room temperature until all the solids completely dissolved. The adhesive composition was spread onto a siliconized PET film 100 µm by means of the scraper so that a dry weight of 80 g/m² was achieved. The solvents were firstly flashed off for ca. 10 minutes at room temperature and then evaporated at ca. 60° C. The laminate was then covered with the heatable fibre material, which was a spun fleece with electrically conductive fibres.

Example 4

Conduct of the Skin Permeation Experiments

For the conduct of the in-vitro permeation tests, a modified diffusion cell in accordance with Keshary-Chien was used. The cell consists of two horizontally divided regions, the donor region and the acceptor region. The temperature of the diffusion cell was maintained at 32° C. by means of a water bath. The acceptor medium (phosphate buffer, pH 5.5) was constantly stirred during the test by means of a magnetic stirrer.

The skin was clamped between the two regions, whereby the stratum corneum of the skin pointed upwards towards the donor region. The plaster was positioned on the skin sample with the adhesive layer towards the stratum corneum of the skin.

The acceptor medium was completely removed from the acceptor region at the specified removal times and kept for the subsequent quantitative determination of the active substance dissolved in it. The same amount of fresh acceptor medium was then added. It was thus ensured that the permeation kinetics are not influenced by potentially reaching the saturation solubility in the acceptor medium.

Dermatomised human skin (800 µm) was used for all the skin permeation experiments. The area of the opening in the cell was 1.54 cm².

The quantitative determination of the active substances permeated into the acceptor medium was effected by means of high performance liquid chromatography (HPLC).

For the analysis of diclofenac, a mixture of acetonitrile and 0.025 m $KH_2PO_4$ (50:50, v/v) was used as the mobile phase. The pH value was set to 3.0. A 150×4.6 mm separation column packed with Zorbax SB C8 80 A 5 µm, was used as the stationary phase. The flow rate was 1.5 ml/min, the column temperature was 30° C. The injection volume was 50 µl, the detector wavelength was set to 225 nm.

For the analysis of ibuprofen, a 150×4.0 mm separation column packed with Novapack C18 5 µm was used. A mixture of acetonitrile:water-tetramethyl:ammonium hydroxide in a mixing ratio of 55:45:1.5 was used as the mobile phase. The pH value was set to 3.0. The flow rate was 1.0 ml/min., the column temperature was 25° C. The injection volume was 50 µl, the detection wavelength was set to 214 nm.

The calculation was effected by means of the External Standard Method using certified reference substances.

The plasters were manufactured so large that their edges projected significantly out of the diffusion cells. The contact to the heatable rear layer was effected by sewn on electrically conductive textile sheets. Direct current (POWER SUPPLY HM 7042-5, from the company HAMEG) was applied to them by means of crocodile clips. In order to achieve a surface temperature of 42° C., the voltage was set to 3V. In order to achieve a 50° C. surface temperature, the voltage was set to 6 V. The resulting current strength was ca. 200 Ma for 3 V and 42° C. and ca. 50 mA for 6V and 50° C.

A parallel measurement without the application of power was effected as a reference.

Figure 1:
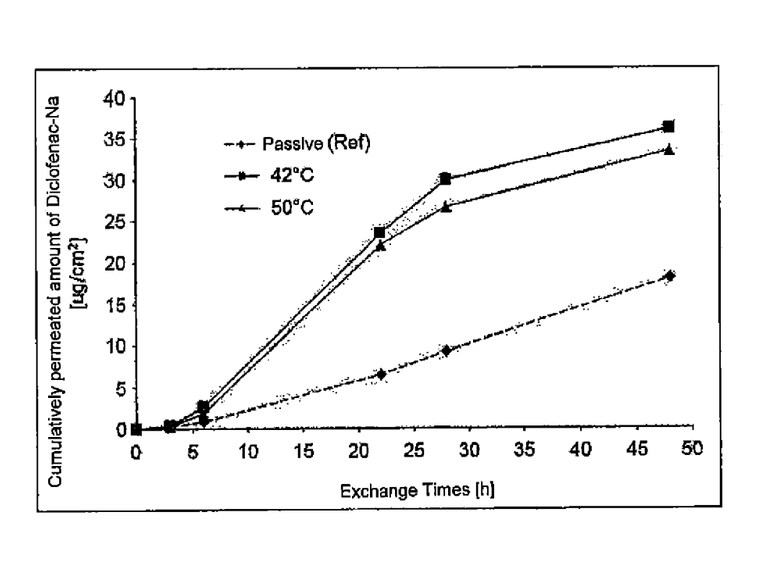
FIG. 1 graphically shows results of skin permeation experiments for diclofenac plastics described in Example 2.

The results of the skin permeation experiments for the diclofenac plastics described in Example 2 are shown graphically in FIG. 1. It is apparent from this illustration that heating the rear layer of the diclofenac plaster to a temperature of about 42° C. or about 50° C. results in a significantly improved permeation of the diclofenac contained in the plaster over the skin compared to the reference referred to as "passive", with which no direct current was applied.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. An electrically heatable plaster comprising:
    a self-adhesive skin contact layer comprising at least one pharmaceutical active substance;
    an electrically conductive, textile sheet comprising a fabric, a knitted structure, a crocheted structure, a braided structure, a bidirectional or multidirectional fabric, a felt, or a fleece of fibers, in which electrically conductive fibers are in contact with one another; and
    wherein the electrically conductive textile sheet is provided with electrical contacts; and
    wherein the electrically conductive textile sheet constitutes a rear layer of the plaster.

2. The plaster as claimed in claim 1;
    wherein the electrically conductive sheet is embedded in a resin layer or polymer layer.

3. The plaster as claimed in claim 2;
    wherein the resin layer or polymer layer includes at least one electrically conductive filler.

4. The plaster as claimed in claim 1;
    wherein the textile sheet comprises:
    a) exclusively electrically conductive fibres;
    b) both electrically conductive fibres and electrically non-conductive fibers; or
    c) at least one electrically non-conductive textile sheet, which is equipped with adhesive, at least one electrically conductive binder, and electrically conductive particles that are fixed three-dimensionally and durably in the textile sheet.

5. The plaster as claimed in claim 1, further comprising:
    a voltage source, preferably a direct current source.

6. The plaster as claimed in claim 1;
    wherein the pharmaceutical active substance comprises at least one substance selected from the group consisting of non-steroidal anti-inflammatory drugs (NSAIDs), anticholinergics, parasympatolytic agents, antimycotics, MAO-B inhibitors, serotonin antagonists, alpha2 receptor agonists, photosensitizers, hormones, and proteins.

7. A method comprising:
    utilizing an electrically conductive textile sheet comprising a fabric, a knitted structure, a crocheted structure, a braided structure, a bidirectional or multidirectional fabric, a felt, or a fleece of fibers, in which electrically conductive fibers are in contact with one another, the electrically conductive textile sheet being provided with electrical contacts, to manufacture the electrically heatable plaster according to claim 1.

8. A method comprising:
utilizing the electrically heatable plaster as claimed in claim 1 in to deliver the at least one pharmaceutical active substance contained in the plaster to a patient.

9. A method comprising:
applying the electrically heatable plaster as claimed in claim 1 to a patient and closing a circuit between a voltage source and the electrically conductive textile sheet.

10. The plaster as claimed in claim 1, further comprising:
a control and regulation electronic system configured to maintain the textile sheet at a constant temperature.

11. A method of manufacturing the electrically heatable plaster as claimed in claim 1, comprising the steps:
providing an electrically conductive textile sheet comprising a fabric, a knitted structure, a crocheted structure, a braided structure, a bidirectional or multidirectional fabric, a felt, or a fleece of fibers, in which electrically conductive fibers are in contact with one another;
laminating the electrically conductive textile sheet onto a self-adhesive skin contact layer comprising at least one pharmaceutical active substance to create a laminate;
separating the laminate into individual plasters; and
applying electrical contacts to the non-laminated side of the electrically conductive textile sheet.

12. The method as claimed in claim 11, further comprising:
providing the laminate with at least one further layer.

\* \* \* \* \*